United States Patent [19]

Montalbano

[11] Patent Number: 4,461,292
[45] Date of Patent: Jul. 24, 1984

[54] COLD WEATHER BREATHING DEVICE WITH IMPROVED CONDUIT AND VALVE ARRANGEMENT

[76] Inventor: Anthony P. Montalbano, 29 Hitching Post La., Glen Cove, N.Y. 11542

[21] Appl. No.: 350,441

[22] Filed: Feb. 24, 1982

Related U.S. Application Data

[63] Continuation-in-part of Ser. No. 239,497, Mar. 2, 1981, Pat. No. 4,441,494.

[51] Int. Cl.³ .............................................. A62B 7/00
[52] U.S. Cl. ........................... 128/204.17; 128/207.16
[58] Field of Search ..................... 128/204.17, 201.13, 128/205.17, 205.24, 206.12, 206.15, 206.21, 206.28, 207.12, 207.16

[56] References Cited

U.S. PATENT DOCUMENTS

| 1,880,998 | 10/1932 | Sturtevant | 128/207.12 |
| 2,505,173 | 4/1950 | Conley | 128/206.15 |
| 3,276,445 | 10/1966 | Langdon | 128/206.15 |
| 3,326,214 | 6/1967 | McCoy | 128/201.13 |
| 3,707,966 | 1/1973 | Nebel | 128/204.17 |

FOREIGN PATENT DOCUMENTS 21424 6/1882 Fed. Rep. of
Germany ........................ 128/204.17

OTHER PUBLICATIONS

"Respiratory Therapy", D. W. Glover, M. M. Glover, The C. V. Mosby Company, St. Louis, 1978, p. 19.

Primary Examiner—Henry J. Recla
Attorney, Agent, or Firm—Frishauf, Holtz, Goodman and Woodward

[57] ABSTRACT

A cold weather breathing device having an improved conduit which has swivel connections and hinge connections, and having an improved dual-flap valve arrangement to reduce vibration and to provide a faster acting valve device. Further disclosed is a deflector baffle arrangement which promotes synchronous valve cycling even under severe conditions and a cool air bypass in the conduit of the device to enable the user to mix cool and warm air so as to provide the desired temperature of the breathed in air.

19 Claims, 11 Drawing Figures

COLD WEATHER BREATHING DEVICE WITH IMPROVED CONDUIT AND VALVE ARRANGEMENT

CROSS-REFERENCE TO RELATED APPLICATION

This is a Continuation-In-Part of my prior U.S. application Ser. No. 239,497, filed Mar. 2, 1981 and now U.S. Pat. No. 4,441,494, the entire contents of which is incorporated herein by reference.

BACKGROUND OF THE INVENTION

This invention relates to cold weather breathing devices, and more particularly to an improved "flexible" conduit arrangement and improved valve arrangements for such devices.

When walking, jogging, running, hunting or carrying out other physical activity in cold weather, one generally has a great deal of discomfort due to the breathing in of very cold air. Additionally, medical problems may be caused due to breathing in cold air when performing physical activities.

When using cold weather breathing devices, for example of the type disclosed in my earlier application Ser. No. 239,497, for walking, jogging and running, it is of utmost important that the user's head has substantially complete freedom of movement so that the user can move his head in substantially any direction, for example to observe automobile traffic. Also, to provide the least possible resistance, the conduit connecting the mouthpiece and the chest covering member should be as short as possible. It is also preferable that the conduit connecting the mouthpiece and the chest covering member not be so flexible (or floppy) that it bounces up and down during running or jogging, for example with a resonance. Theoretically, a substantially rigid conduit would be preferable from the point of view of vibration and stability of the conduit. However, such a rigid conduit would not provide the flexibility required to permit substantially free movement of the head of the user.

It has been found that cold air breathing devices with large valves for directing air flow sometimes cause vibrations which are transferred to the mouth and which could hurt the user's teeth when running. Moreover, it has been found that when the user exhausts air with maximum force, a vacuum is sometimes created in the chamber between the intake and exhaust valves which could lift both intake valves off of their seats. This disadvantageously causes air to bleed back into the intake pipe.

An object of the present invention is to provide an improved cold air breathing device having faster acting valves which provide less resistance to air flow and which reduces the tendency to produce disadvantageous vibrations.

A further object of the invention is to provide such a cold weather breathing device with a means for preventing a vacuum from being created in the chamber between the intake and exhaust valves in order to prevent exhaust air from bleeding back into the intake pipe of the device. Such a means would also promote a better synchronous valve cycle under mild and severe exhaust conditions.

Another object of the present invention is to provide an improved conduit arrangement for a cold air breathing device which uses body heat to heat the inhaled air, and which is simple in construction, easy to manufacture, and which permits substantially free movement of the head of the user without excessively vibrating and bobbing up and down.

A further object is to provide such a device which, while providing substantially free mobility of the head, also has characteristics associated with a rigid or substantially rigid conduit.

Still another object is to provide such a conduit which can be fabricated advantageously with simple molded plastic parts.

Yet another object is to provide a conduit which does not utilize corrugated flexible portions, which corrugations tend to restrict air flow.

SUMMARY OF THE INVENTION

A cold weather breathing device comprises a mouthpiece which is insertable in the mouth of a user and which substantially provides a seal to the mouth of the user; a conduit extending downwardly from the mouthpiece and in air communication with the mouthpiece; a first valve in air communication with the conduit and mouthpiece for communicating the conduit and mouthpiece when the user inhales, and for blocking the communication between the conduit and mouthpiece when the user exhales; an exhaust opening coupled to the mouthpiece for exhausting exhaled air to the atmosphere; a second valve coupled between the exhaust opening and the mouthpiece for providing air communication between the mouthpiece and the exhaust opening when the user exhales, and for blocking the air communication between the exhaust opening and mouthpiece when the user inhales; and a heat exchange unit adapted to be placed adjacent a chest area of a user, the heat exchange unit being coupled to an end portion of the conduit remote from the mouthpiece, and providing at least one air passage in air communication with the interior of the conduit. In accordance with a feature of the present invention, an improvement in the above-described device resides in that the conduit which extends from the mouthpiece to the heat exchange unit comprises at least one swivel joint in the vicinity of the heat exchange and about which said conduit is pivotable around its longitudinal axis; at least one pivot joint adjacent said swivel joint about which the conduit is pivotable about an axis perpendicular to the longitudinal axis of the conduit; and at least one second pivot joint in the vicinity of the mouthpiece and about which said conduit is pivotable about an axis perpendicular to the longitudinal axis of the conduit. The intermediate section of the conduit, between the two pivot joints, may comprise a rigid section or a bellows section. Preferably, a rigid section is provided between the pivot joints to provide the best structural integrity. An adjustable connection can be provided in the intermediate section to adjust the length of the intermediate section of the conduit for different physical characteristics of various users of the device. Such an adjustment can be provided in the intermediate section by making the intermediate section a telescoping section.

According to a further feature of the invention, an improvement in the above-described device resides in that the first and second valves are comprised of two pivotable valve members, each preferably a flap-type valve. The two pivotable valve members of each valve are preferably located adjacent each other. By increasing the number of valve members for each respective valve, the valves can open and close in a much faster cycle, with much less resistance to air flow. Moreover, since each valve member has a smaller size and is of less weight than the single valve member, vibrations are reduced, thereby improving the comfort of the user.

In accordance with a further feature of the invention, at least one deflector member is arranged adjacent the mouthpiece and adjacent the first valve and in the path of exhausted exhaled air for deflecting or diverting a portion of the exhaust air to impinge on flaps of the first valve to positively prevent opening of the first valve during exhaust cycles.

DETAILED DESCRIPTION

Figure 1:
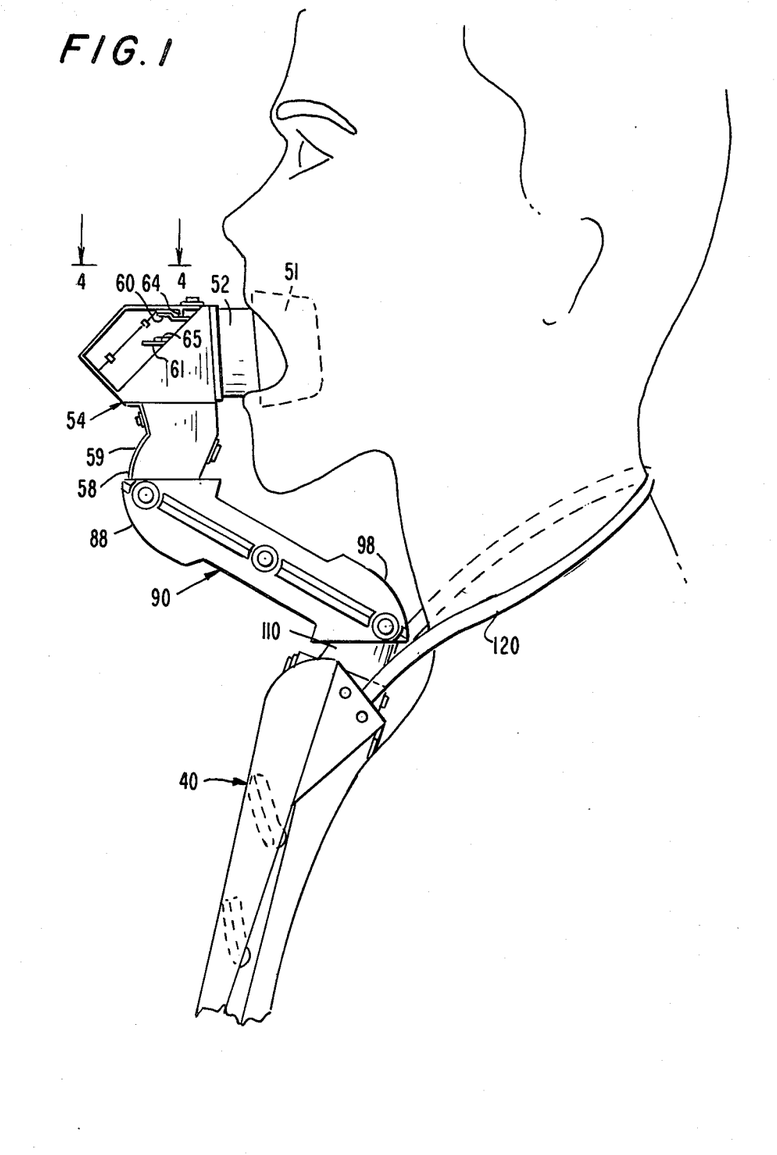
FIG. 1 is a side view of the device of the present invention.
Figure 2:
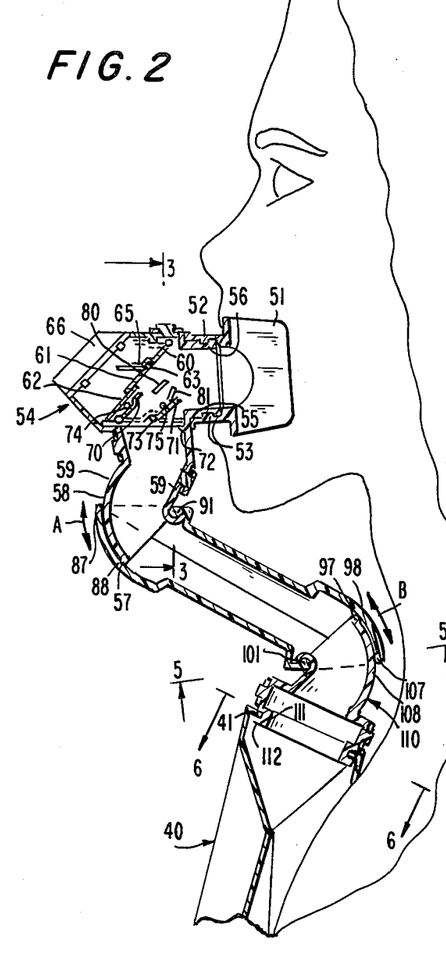
FIG. 2 is a side elevational view of the device of FIG. 1, showing the valves in solid lines in the inhale position, and showing the valves in dashed lines in the exhale position.
Figure 3:
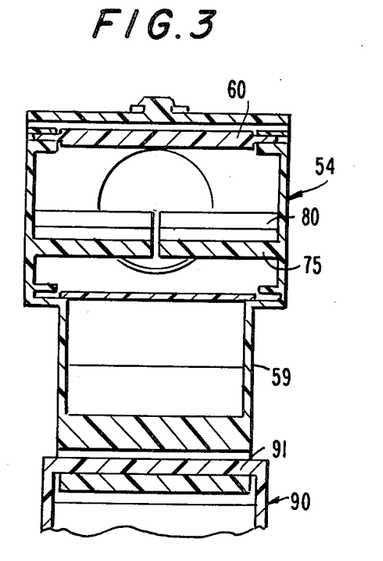
FIG. 3 is a sectional view taken along line 3—3 in FIG. 2.
Figure 4:
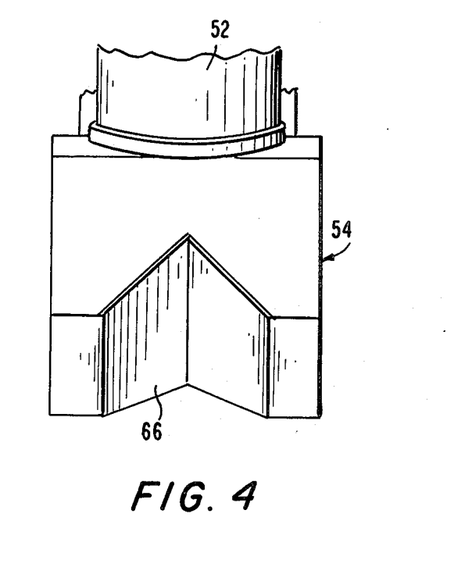
FIG. 4 is a top view of the mouthpiece portion of the device taken in the direction of lines 4—4 in FIG. 1.
Figure 5:
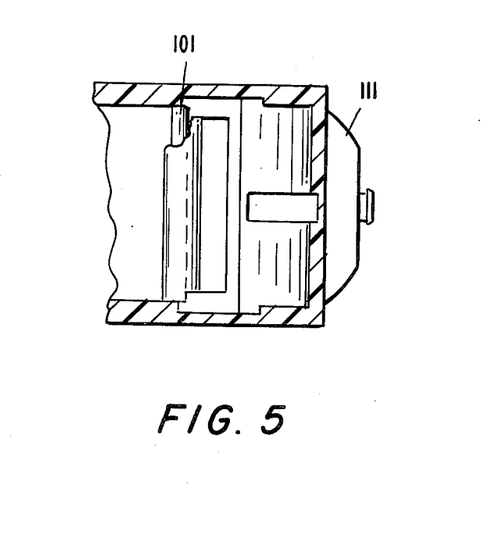
FIG. 5 is a sectional view taken along line 5—5 in FIG. 2.

Referring to FIGS. 1-3, the device of the present invention comprises a mouthpiece 51 having a generally cylindrical extension member 52 extending out of the mouth of the user. The extending member 52 has a protrusion 53 along the inner surface thereof, preferably around the complete inner peripheral surface of extending member 52. A housing 54 has a generally cylindrical extension 55 which fits within cylindrical extension 52 with a small clearance therebetween to permit the housing 54 to be rotatable about the mouthpiece 1. The housing extension 55 has a groove or cut-out portion 56, preferably extending around the periphery thereof which receives protrusion 53 of the extension 52 of the mouthpiece 51. By virtue of this arrangement, the housing 54 and the mouthpiece 51 are rotatable relative to each other about the horizontal axis as seen in FIG. 2.

The housing 54 contains a pair of exhaust valves 60, 61 which are shown in solid lines in the inhale position, and which are shown in dashed lines in the exhaust or exhale position. The housing 54 has a member 62 which serves as a seat for flap valve 61, the pivotable portions 63 of flap valve 61 comprising the seat for flap valve 60. Abutment members 64, 65 are provided to serve as stop members for the flap valves 60, 61, respectively, when they are in their respective open position. The housing 54 further has an opening 66 which opens to the atmosphere to exhaust air.

Flap valves 70, 71 of the intake or inhale valve arrangement are shown in solid lines in the open or inhale position, and are shown in dashed lines in their closed or exhale position. A seat 72 is formed in the housing 54 for flap valve member 71, the pivotable portion 73 of flap valve 71 serving as the seat for flap valve member 70. Abutment members 74, 75 span across housing 54 and serve as stop members for the flap valve members 70, 71, respectively, when the flaps 70, 71 are in their open position, as shown by solid lines in FIG. 2.

By arranging the intake valve arrangement as two small flap-valves 70, 71, and by arranging the exhaust valve as two individual valve flaps 60, 61, instead of single flap valves respectively as shown in my copending application Ser. No. 239,497, filed Mar. 2, 1981, the valves are smaller and are of less weight, and can therefore open and close in a much faster cycle with much less resistance to air flow. In the valve of my copending application Ser. No. 239,457, the circumferential travel arc of the individual flap valves was about one inch. In the valve arrangement of the present invention, each individual flap can travel only about one-half inch, and provide effectively the equivalent results to the single valve of my copending application. Since the valves of the present invention are half the size and half the weight of the prior single flap arrangement, a major vibration source is eliminated or substantially reduced. Thus, vibrations which would pass through the mouthpiece and hurt the teeth of the user are virtually eliminated or substantially reduced.

Located within the housing 54 are deflectors 80, 81 which deflect a portion of the exhaust air from the mouth of a user during the exhale cycle downward against the flap valves 70, 71. During the exhaust sequence, it is desired that the flap valves 70, 71 remain closed in order to effectively prevent exhaust air from travelling downward through exhaust valves 70, 71. However, when one is at the end of the jogging run, or in any situation where there is a tendency to exhaust air with maximum force, a vacuum is sometimes created in the chamber 54 between the intake and exhaust valves which lifts both intake valves off their respective seats. This causes exhaust air to bleed back into the intake pipe 90, which effect is extremely disadvantageous. According to the present invention, the baffle plates 80, 81 are arranged to divert part of the exhaust air downwardly to impinge on the closed inlet flaps 70, 71 during the exhaust cycle. This impingement of exhaust air on the flaps 70, 71 maintains the flaps 70, 71 closed and prevents bleeding of exhaust air downwardly through the pipe 90. This also promotes a highly synchronous valve cycle under both mild and severe exhaust conditions.

The design of the inlet and exhaust valves, in combination with the deflector plates 80, 81, as described above, enables a massive exchange of air as generated by a runner under stress, with a minimum restrictive back pressure and a maximum air exchange. Preferably, the deflector plates 80, 81 deflect about 10% of the exhaust (exhale) air toward the closed flaps 70, 71.

Pivotally connected to the housing 54 is a conduit 90, which in the illustrated embodiment of FIG. 2 is a substantially rigid conduit. The pivotal connection comprises a pivot point 90 about which the housing extension 59 is pivotally connected to the conduit 90. The housing extension 59 and conduit 90 have arcuate portions 58, 88, respectively, which slide relative to each other as member 90 pivots about pivot point 91 relative to housing extension 59. Arcuate portion 88 has an abutment member 87 at the end thereof which bears on the outer surface of arcuate portion 58. Arcuate portion 58 has an abutment member 57 at the end thereof which abuts against the inner surface of arcuate portion 88. The abutments 87, 57 retain the members engaged with each other and help prevent leakage of air into and out of the connection between housing extension 59 and conduit 90. As a result, a substantially airtight pivotable connection is achieved in a simple manner.

A similar pivotable connection is provided at the lower end of conduit 90. Conduit 90 is connected to a connecting member 110 at pivot point 101. Connecting member 110 has an arcuate surface 108 which is in registration with lower arcuate surface 98 of conduit 90. Respective abutment-type retaining and sealing members 97, 107 are provided which are similar in construction and effect to abutment sealing members 87, 57 described above. By virtue of this arrangement, the lower portion of conduit 90 is pivotable relative to connecting member 110 about lower pivot point 101.

FIG. 3 illustrates the pivotable connection at the upper portion of conduit 90 in greater detail. The pivotable connection at the lower portion of conduit 90 is identical.

Figure 6:
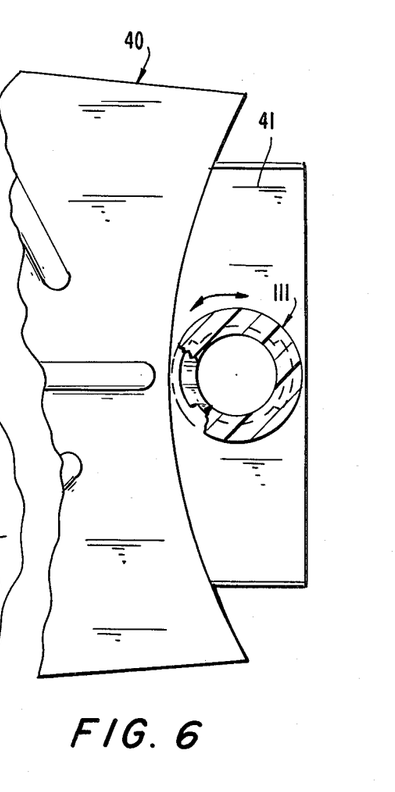
FIG. 6 is a sectional view taken along line 6—6 in FIG. 2.

Connecting member 110 is rotatably connected to the shield unit 40, which may be substantially identical to the shield unit of copending application Ser. No. 239,497, except for the portion where it connects to connecting member 110, which connecting portion will be described in detail below. Shield member 40 comprises an inwardly projecting member 41 which is preferably generally cylindrical, as seen in FIG. 6. The connecting member has a lower cylindrical portion 111 with a notch 112 formed therein for receiving projection 41 of the shield member 40. By virtue of this arrangement, shield member 40 is rotatably connected to connecting member 110.

With the above arrangement, substantially complete freedom of movement is provided to the user since for any head movement, the respective rotatable and pivotable connections illustrated in FIG. 2 enable the device to follow the user's head motion and conform in shape thereto with very little, if any, resistance to head motion. By virtue of the sealing members, and groove-type rotatable connections, a substantially air-tight connection is achieved at all rotatable and/or pivotable connecting points.

As seen in FIG. 1, a neck strap 120 is provided to wrap around the neck of the user to help anchor the breathing device in position.

Figures 7, 10:
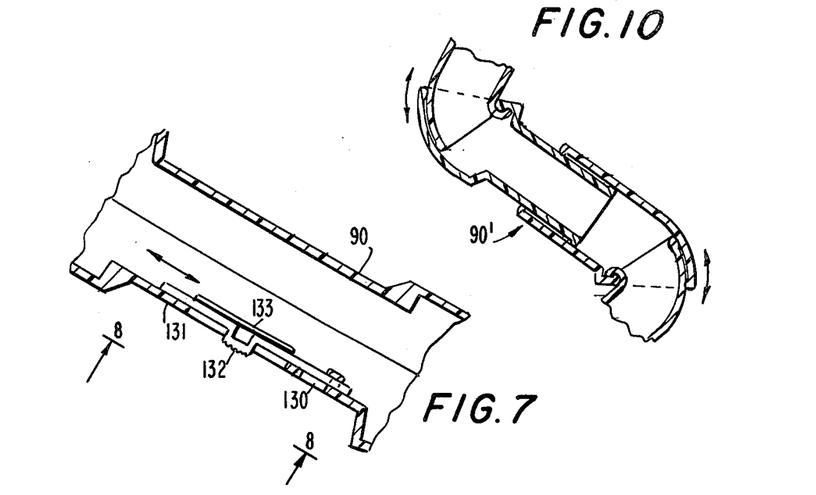
FIG. 7 is a partial sectional view of a modified conduit of the present invention having an adjustable opening therein.
FIG. 10 illustrates a telescoping conduit.

FIG. 10 illustrates a telescoping conduit section to provide further adjustability of the device of the present invention. The telescoping arrangement is self-evident and a further description thereof is deemed unnecessary.

Figure 8:
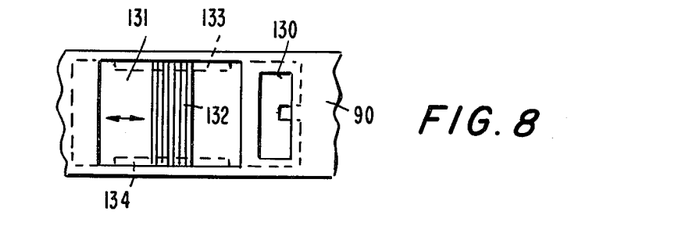
FIG. 8 is a front view of the section of the conduit in FIG. 7 having the adjustable opening therein.
Figure 9A:
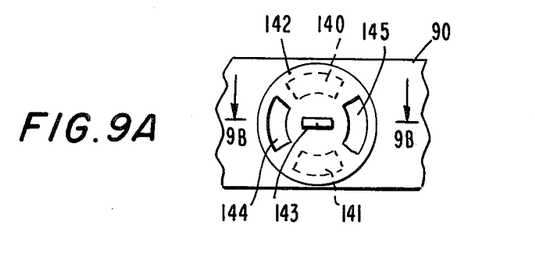
FIGS. 9a and 9b are front and sectional views, respectively, of a modified opening for the conduit shown in FIG. 7.
Figure 9B:
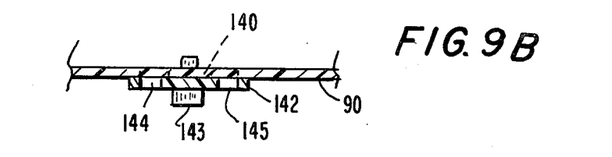

Referring to FIGS. 7-9, a modified arrangement of the conduit 90 is shown. As illustrated in FIGS. 7-9, a fresh air bypass is located in the conduit 90. The bypass is preferably adjustable, and can be a sliding type arrangement (FIGS. 7 and 8) or a rotary arrangement as shown in FIG. 9. It has been found that after jogging or running for a period of time, the breathed-in air may get very warm. The bypass illustrated in FIGS. 7-9 provides a means to cool the incoming air for optimum comfort of the user. The bypass is preferably located in the neck duct 90 to provide good mixing prior to inhaling of the air. For example, if the jogger overdresses and thereby restricts the air flowing in around the shield member 40 (FIG. 1), the bypass shown in FIGS. 7-9 provides an alternative means for breathing in semi-warm air without taking the mouthpiece out of his mouth. By adjusting the degree of opening of the bypass of FIGS. 7-9, cool external air is mixed with warm air from the shield 40, as desired.

As seen in FIGS. 7 and 8, the bypass comprises an opening area 130 which may be selectively closed by means of a slideable member 131 having a serrated operating button-like member 132 projecting outwardly of the duct 90. The slideable member 131 is retained in position by means of the button-like operating member 132 overlying an edge 133, 134 of the conduit 90, as seen in FIG. 8. A stop member 135 is provided to define the closed position of the opening 130.

FIGS. 9a and 9b illustrate a rotary type arrangement wherein the conduit 90 comprises openings 140, 141 which are preferably sector-shaped. A rotatable disc-like closure member 142 is rotatably mounted to the conduit with an operating handle 143 extending therefrom, as best seen in FIG. 9b. As the disc 142 is rotated, sector-shaped openings 144, 145 therein are brought into selective registration with sector-shaped openings 140, 141 in the conduit 90. As the disc member 142 is rotated further, the opening is increased. FIG. 9a illustrates the disc 142 in the position whereby the openings 140, 141 of the conduit 90 are completely closed.

Below is a brief summary of some of the important features of the device of the present invention.

The short distance between the mouthpiece to the chest pad is critical to an optimum low back pressure and high air flow condition when used in conjunction with joggers and runners who, under stress, require a high air flow plus minimum restriction to air flow. To insure totally free head movement as well as adjustment to various body configurations plus low air back pressure and high air flow, the device of the invention:

a. minimizes the distance between mouthpiece and chest pad;
b. eliminates the need for a long corrugated air hose (to achieve the same head movement). The corrugated hose-pleats also tend to restrict air flow; and
c. provides substantially totally free head rotation and movement for runner safety when approaching intersection looking at road, or moving head in every possible position to insure universal vision.

The pivotable airtight conduit of the invention can be described as providing the head with total extreme vertical movement (up and down) plus horizontal (left to right) movement via the axial swivel located at the top of the chest pad 40. The combination of the radial and axial movement as applied to this warm air breathing device provides the runner or jogger with an oral shock absorber, by dampening the opposing jerking motions evident when running, between the chest pad 40 and mouthpiece 54. When a person runs or jogs, the body mechanism automatically maintains the total head in a reasonably stable position relative to the ground, while the chest and the rest of the body jerks and jolts with each running stride. The dampening effect of this concept not only enables the runner to maintain a steady head and vision posture, but it also prevents the jaw and teeth from aching due to the excessive jolts and shocks of running.

Still further, the deflector baffles 80, 81 divert part of the exhaust air downwardly to impinge on the inlet flaps during the exhaust cycle. This impingement prevent bleeding of exhausted air and promotes a highly synchronous valve cycle under mild and severe exhaust conditions. Still further, as discussed with respect to FIGS. 7-9b, the device of the present invention provides a cool air bypass to prevent discomfort due to breathing in overly warm air.

I claim:

1. In a cold weather breathing device comprising a mouthpiece which is insertable in the mouth of a user; a conduit connected to said mouthpiece and extending downwardly from the mouthpiece and being in air communication with the mouthpiece; a first valve means in air communication with said conduit and mouthpiece for providing air communication between said conduit and said mouthpiece when the user inhales, and for blocking said air communication between said conduit and mouthpiece when the user exhales; an exhaust opening coupled to the mouthpiece for exhausting exhaust air to the atmosphere; a second valve means coupled between said exhaust opening and said mouthpiece for providing air communication between said mouthpiece and said exhaust opening when the user exhales, and for blocking said air communication between said exhaust opening and mouthpiece when the user inhales; and means coupled to said conduit at the opposite end thereof from said mouthpiece and adapted to communicate with the body of a user for collecting heat from said body of said user and transferring said heat into the air flowing into said conduit;

the improvement comprising:
at least one swivel joint coupling the conduit to said means for supplying warmed air, and about which said conduit is rotatable;
at least one first pivot joint adjacent said swivel joint and about which said conduit is pivotable about an axis perpendicular to the longitudinal axis of the conduit; and
at least one second pivot joint in the vicinity of the mouthpiece end of said conduit and about which said conduit is pivotable about an axis perpendicular to the longitudinal axis of said conduit.

2. The breathing device of claim 1 wherein said conduit comprises a substantially rigid section between said pivot joints.

3. The breathing device of claim 1 or 2, further comprising a swivel joint connecting said mouthpiece to said conduit.

4. The breathing device of claim 1, wherein said conduit comprises a main central section and a pair of pivotable sections at opposite ends of said main section, said pivot joints each comprising a pivot connection between said main section of said conduit and one of said pivotable members of said conduit on one side of said conduit, and a relatively slideable area therebetween on the other side of said conduit.

5. In a cold weather breathing device comprising a mouthpiece which is insertable in the mouth of a user; a conduit connected to said mouthpiece and extending downwardly from the mouthpiece and being in air communication with the mouthpiece; a first valve means in air communication with said conduit and mouthpiece for providing air communication between said conduit and said mouthpiece when the user inhales, and for blocking said air communication between said conduit and mouthpiece when the user exhales; an exhaust opening coupled to the mouthpiece for exhausting exhaust air to the atmosphere; a second valve means coupled between said exhaust opening and said mouthpiece for providing air communication between said mouthpiece and said exhaust opening when the user exhales, and for blocking said air communication between said exhaust opening and mouthpiece when the user inhales; and means coupled to said conduit at the opposite end thereof from said mouthpiece and adapted to communicate with the body of a user for collecting heat from said body of said user and transferring said heat into the air flowing into said conduit;

the improvement comprising:
said first valve means includes first and second pivotable valve members located adjacent each other;
said second valve means includes first and second pivotable valve members located adjacent each other;
whereby said first and second pivotable valve members of said first and second valve means provide faster valve switching action and vibrations are reduced; and
at least one deflector member arranged adjacent said mouthpiece and adjacent said first and second pivotable valve members of said first valve means and in the path of exhausted exhaled air directed toward said second valve means to impinge exhaled air on said pivotable valve members of said first valve means to positively prevent opening of said first valve means during exhaust cycles, thereby preventing bleeding of exhaust air into said conduit during exhaust cycles and promoting improved synchronous operation of said first and second valve means.

6. The breathing device of claim 5 comprising at least two of said deflector members.

7. The breathing device of claim 5, wherein said at least one deflector member deflects about 10% of the exhaust air towards said first valve means.

8. The breathing device of claim 1 wherein said first valve means includes at least one pivotable valve member, and further comprising at least one deflector member arranged adjacent said mouthpiece and adjacent said first valve means and in the path of exhausted exhaled air for deflecting or diverting a portion of the exhaust air to impinge on said at least one pivotable valve member of said first valve means to positively prevent opening of said first valve means during exhaust cycles.

9. The breathing device of claim 8 comprising at least two of said deflector members.

10. The breathing device of claim 8 or 9, wherein said at least one deflector member deflects about 10% of the exhaust air towards said first valve means.

11. In a cold weather breathing device comprising a housing defining inhalation and exhalation flowpaths; a mouthpiece connected to said housing and which is insertable in the mouth of a user; a conduit connected to said housing and extending downwardly from the housing and being in air communication with the mouthpiece; a first valve means in air communication with said conduit and mouthpiece for providing air communication between said conduit and said mouthpiece through said inhalation flowpath when the user inhales, and for blocking said air communication between said conduit and mouthpiece when the user exhales; an exhaust opening coupled to the housing for exhausting exhaust air to the atmosphere; a second valve means coupled between said exhaust opening and said mouthpiece for providing air communication between said mouthpiece and said exhaust opening through said exhalation flowpath when the user exhales, and for blocking said air communication between said exhaust opening and mouthpiece when the user inhales; and means coupled to said conduit at the opposite end thereof from said housing and adapted to communicate with the body of a user for collecting heat from said body of said user and transferring said heat into the air flowing into said conduit;
the improvement comprising:
said first valve means being out of the exhalation flowpath and at least one deflector member arranged adjacent said mouthpiece and adjacent said first valve means and in the exhalation flowpath of exhausted exhaled air directed toward said second valve means for deflecting or diverting a portion of said exhaled exhaust air toward said first valve means to impinge on said first valve means to positively prevent opening of said first valve means during exhaust cycles, thereby preventing bleeding of exhaust air into said conduit during exhaust cycles and promoting improved synchronous operation of said first and second valve means.

12. The breathing device of claim 11 comprising at least two of said deflector members.

13. The breathing device of claim 11 or 12, wherein said at least one deflector member deflects about 10% of the exhaust air towards said first valve means.

14. The breathing device of any one of claims 1, 5, or 11 further comprising variable opening means coupled to an intermediate portion of said conduit for permitting atmospheric air to enter said conduit so as to be mixed with warmed air supplied by said means for supplying warmed air.

15. A cold weather device comprising:
a mouthpiece which is engageable only with the mouth area of a user and which is insertable in the mouth of the user, said mouthpiece not extending to the nose of the user and leaving the nose of the user uncovered;
a valve housing coupled to said mouthpiece and in air communication with only the mouth of the user via said mouthpiece, and being out of air communication with the nose of the user;
a conduit coupled to an extending downwardly from said valve housing and in selective air communication with said mouthpiece via said valve housing;
a first valve in said valve housing and in air communication with said conduit and mouthpiece for providing an air communication path between said conduit and said mouthpiece when the user inhales, and for blocking said air communication path between said conduit and mouthpiece when the user exhales;
an exhaust opening in said valve housing and being in selective air communication with said mouthpiece for selectively exhausting exhaled air to the atmosphere;
a second valve in said valve housing and coupled between said exhaust opening and said mouthpiece for providing an air communication path between said mouthpiece and said exhaust opening when the user exhales, and for blocking said air communication path between said exhaust opening and mouthpiece when the user inhales; and
a shield unit having a top end, opposite sides, a bottom end, an inner surface, an outer surface and a substantially central portion, said shield unit including a substantially air impervious shield member coupled to an end portion of said conduit remote from said mouthpiece and a first and second plurality of spaced apart projecting members extending from said inner surface of said shield member and adapted to abut against the body of a user, said projecting members defining with said shield member, when placed against the body of a user, a plurality of substantially unrestricted air passages, said first plurality of projecting members being on one side of said substantially central portion of said shield unit and defining first substantially unrestricted air passages extending from around a side periphery of said shield member to said substantially central portion of said shield member, said second plurality of projecting member being on the other side of said substantially central portion of said shield unit and defining second substantially unrestricted air passages extending from around the other side periphery of said shield member to said substantially central portion of said shield member, a substantially central air passage being defined at said substantially central portion of said shield member between said first and second pluralities of projecting members, and said shield unit further including guide means at least at the top end of said shield unit for guiding air from said air passages to said substantially central air passage and to prevent air from passing out of said shield unit at the top end except through said conduit, said substantially central air passage being in substantially unrestricted air communication with said first and second substantially unrestricted air passages, said first and second substantially unrestricted air passages substantially unrestrictedly opening to side peripheries of said shield unit and extending substantially unrestrictedly from at least said openings at said side peripheries of said shield unit to said substantially central air passage, said shield unit being coupled to said conduit such that said first and second substantially unrestricted air passages are in substantially unrestricted air communication with the interior of said conduit via said substantially central air passage to provide substantially unrestricted flow of air from the periphery of said shield unit to the interior of said conduit and to said mouthpiece, whereby said shield unit is adapted to be placed against a body portion of a user to provide substantially unrestricted open-ended air flow through said first and second substantially unrestricted air passages, said substantially central air passage and to said mouthpiece via said conduit whereby the body heat of the user heats cold air passing therethrough.

16. The cold weather breathing device of claim 15, wherein said first plurality of projecting members extend from one of said opposite sides of said shield unit; and wherein said second plurality of projecting members extend from the other of said opposite sides of said shield unit.

17. A cold weather breathing device comprising:
a mouthpiece which is insertable in the mouth of a user;
a conduit coupled to said mouthpiece, said conduit extending downwardly from said mouthpiece and being in air communication with said mouthpiece;
a first valve in air communication with said conduit and said mouthpiece for providing air communication between said conduit and said mouthpiece when the user inhales, and for blocking said air communication between said conduit and mouthpiece when the user exhales;

an exhaust opening coupled to said mouthpiece for exhausting exhaled air to the atmosphere;

a second valve coupled between said exhaust opening and said mouthpiece for providing air communication between said mouthpiece and said exhaust opening when the user exhales, and for blocking said air communication between said exhaust opening and mouthpiece when the user inhales; and a shield unit having a top end, opposite sides, a bottom end, an inner surface, an outer surface and an intermediate portion, said shield unit including a substantially air impervious shield member coupled to an end portion of said conduit remote from said mouthpiece and a first and second plurality of spaced apart projecting members extending from said inner surface of said shield member and adapted to abut against the body of a user, said projecting members defining with said shield member, when placed against the body of a user, a plurality of substantially unrestricted air passages, said first plurality of projecting members being on one side of said intermediate portion of said shield unit and defining first substantially unrestricted air passages extending from around a side periphery of said shield member to said intermediate portion of said shield member, said second plurality of projecting members being on the other side of said intermediate portion of said shield unit and defining second substantially unrestricted air passages extending from around the other side periphery of said shield member to said intermediate portion of said shield member, an intermediate air passage being defined between said first and second pluralities of projecting members, said shield unit further including guide means at least at the top end of said shield unit for guiding air from said air passages to said substantially central air passage and to prevent air from passing out of said shield unit at the top end except through said conduit, said intermediate air passage being in substantially unrestricted fluid communication with said first and second substantially unrestricted air passages, said substantially unrestricted air passages substantially unrestrictedly opening to the side peripheries of said shield unit and extending substantially unrestrictedly from at least said openings at said side peripheries of said shield unit to said intermediate air passage, said shield unit being coupled to said conduit such that said first and second substantially unrestricted air passages are in substantially unrestricted air communication with the interior of said conduit via said intermediate air passage to provide substantially unrestricted flow of air from the periphery of said shield unit to the interior of said conduit and to said mouthpiece, whereby said shield unit is adapted to be placed against a body portion of a user to provide substantially unrestricted open-ended air flow through said first and second substantially unrestricted air passages, said intermediate air passage and to said mouthpiece via said conduit whereby the body heat of the user heats cold air passing therethrough.

18. The cold weather breathing device of claim 17, wherein said first plurality of projecting members extend from one of said opposite sides of said shield unit; and wherein said second plurality of projecting members extend from the other of said opposite sides of said shield unit.

19. The cold weather breathing device of claim 17, wherein said intermediate portion of said shield unit is a substantially central portion of said shield unit.

* * * * *

UNITED STATES PATENT AND TRADEMARK OFFICE
CERTIFICATE OF CORRECTION

PATENT NO. : 4,461,292
DATED : July 24, 1984
INVENTOR(S) : Anthony P. Montalbano It is certified that error appears in the above-identified patent and that said Letters Patent is hereby corrected as shown below:

The term of this patent subsequent to April 10, 2001, has been disclaimed.

Signed and Sealed this

Third Day of September 1985

[SEAL]

Attest:

DONALD J. QUIGG

*Attesting Officer*   *Acting Commissioner of Patents and Trademarks - Designate*